United States Patent
Li et al.

(10) Patent No.: US 10,836,751 B2
(45) Date of Patent: Nov. 17, 2020

(54) METHODS FOR PREPARING NINTEDANIB AND INTERMEDIATES THEREOF

(71) Applicants: Zhejiang Huahai Pharmaceutical Co., Ltd., Zhejiang (CN); Shanghai Syncores Technologies, Inc., Shanghai (CN)

(72) Inventors: Zeng Li, Shanghai (CN); Xiaosong Cheng, Shanghai (CN); Xianliang He, Shanghai (CN); Jicheng Zhang, Shanghai (CN); Luning Huang, Shanghai (CN); Anping Tao, Shanghai (CN); Hong Gu, Shanghai (CN)

(73) Assignees: Zhejiang Huahai Pharmaceutical Co., Ltd., Zhejiang (CN); Shanghai Syncores Technologies, Inc., Shanghai (CN)

( * ) Notice: Subject to any disclaimer, the term of this patent is extended or adjusted under 35 U.S.C. 154(b) by 0 days.

(21) Appl. No.: 16/339,339

(22) PCT Filed: Oct. 11, 2017

(86) PCT No.: PCT/CN2017/105723
§ 371 (c)(1),
(2) Date: Apr. 3, 2019

(87) PCT Pub. No.: WO2018/068733
PCT Pub. Date: Apr. 19, 2018

(65) Prior Publication Data
US 2020/0048225 A1    Feb. 13, 2020

(30) Foreign Application Priority Data

Oct. 12, 2016  (CN) .......................... 2016 1 0890758
Oct. 13, 2016  (CN) .......................... 2016 1 0891645

(51) Int. Cl.
*C07D 209/34*   (2006.01)
*C07D 403/12*   (2006.01)

(52) U.S. Cl.
CPC .......... *C07D 403/12* (2013.01); *C07D 209/34* (2013.01)

(58) Field of Classification Search
CPC .................................................... C07D 209/34
See application file for complete search history.

(56) References Cited

FOREIGN PATENT DOCUMENTS

| CN | 101883756 | 11/2010 |
|---|---|---|
| CN | 104262232 | 1/2015 |
| CN | 105461609 | 4/2016 |
| WO | WO 2012/068441 | 5/2012 |
| WO | WO 2016/178064 | 11/2016 |

OTHER PUBLICATIONS

Ahava et al. Synthetic Communications vol. 47, No. 10 p. 975-981. (Year: 2017).*
International Search Report of PCT/CN2017/105723 dated Jan. 15, 2018 (2 pages) (English translation).
Liu et al., "Graphical Synthetic Routes to Nintedanib", Chinese Journal of Medicinal Chemistry), non-official translation Apr. 30, 2016, 26(2), pp. 154-156, 3 pages.

* cited by examiner

*Primary Examiner* — Emily A Bernhardt
(74) *Attorney, Agent, or Firm* — Sheppard Mullin Richter & Hampton LLP

(57) ABSTRACT

The present application provides a method for preparing nintedanib. The method of the present application is carried out by using 4-halo-3-nitro-benzoic acid methyl ester (compound II) and 3-oxo-3-phenylpropionate (compound III) as raw materials, and preparing nintedanib via intermediates of methyl 4-(1-alkoxy-1,3-dioxo-3-phenyl propan-2-yl)-3-nitrobenzoate (compound IV) and methyl 3-benzoyl-2-oxoindoline-6-formate (compound V). The method for preparing nintedanib (I) provided by the present application has the advantages of using easily obtained raw materials, having a simple process, being cost effective and environmentally friendly, and is suitable for industrial-scale production.

7 Claims, No Drawings

METHODS FOR PREPARING NINTEDANIB AND INTERMEDIATES THEREOF

CROSS REFERENCE TO RELATED APPLICATIONS

The present application is a national stage application of International Application PCT/US2017/105723, filed Oct. 11, 2017, which application claims priority to Chinese Patent Application No. 201610890758.6, filed Oct. 12, 2016 and Chinese Patent Application 201610891645.8, field Oct. 13, 2016, the contents of which are incorporated by reference in their entireties into the present disclosure.

TECHNICAL FIELD

The present application pertains to the technical fields of organic synthesis and preparation of bulk drug intermediates, in particular to a preparation method of the drug nintedanib prepared for treating idiopathic pulmonary fibrosis, key intermediates thereof and preparation methods of the key intermediates.

BACKGROUND OF ART

Nintedanib is a new oral drug developed by Boehringer Ingelheim for treating idiopathic pulmonary fibrosis. Idiopathic pulmonary fibrosis is a fatal lung disease that is severely harmful to humans. The median survival time of the patients is only 2 to 3 years after diagnosis.

Nintedanib can simultaneously block vascular endothelial growth factor receptor, platelet-derived growth factor receptor and fibroblast growth factor receptor. Blocking of these receptors leads to inhibition of angiogenesis. Nintedanib is the first and only tyrosine kinase inhibitor approved for treating idiopathic pulmonary fibrosis.

The chemical name of Nintedanib is methyl Z-[1-(4-(N-((4-methyl-piperazin-1-yl)-methylcarbonyl)-N-methyl-amino)-anilino)-1-phenyl-methylene]-2-oxo-2,3-dihydro-1H-indole-6-formate, which is shown in the following formula I:

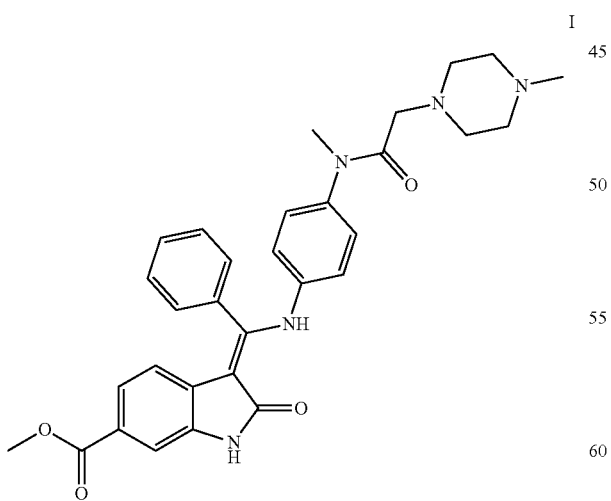

The preparation methods of nintedanib have already been reported and the synthesis methods of nintedanib and its analogs are given by the original compound patent WO2001027081 and the preparation patents WO2009071523 and WO2009071524. The synthetic methods are mainly with respect to the condensation of two key intermediates A and B as described in the following procedure. Wherein, the synthesis route of intermediate A is relatively long, the preparation yield of compound 1-3 is low, cyclization reaction of compound 1-4 requires hydrogenation under high temperature and high pressure and the preparation of compound A requires high temperature. The route is costly and complicated to operate.

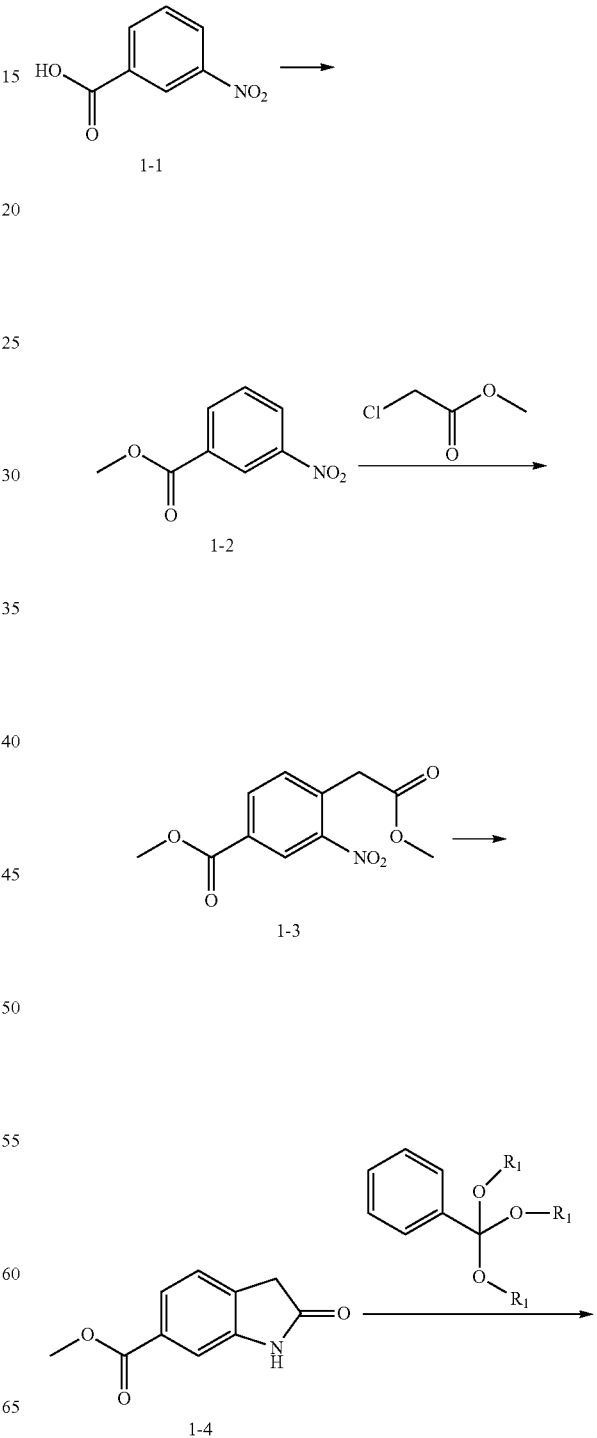

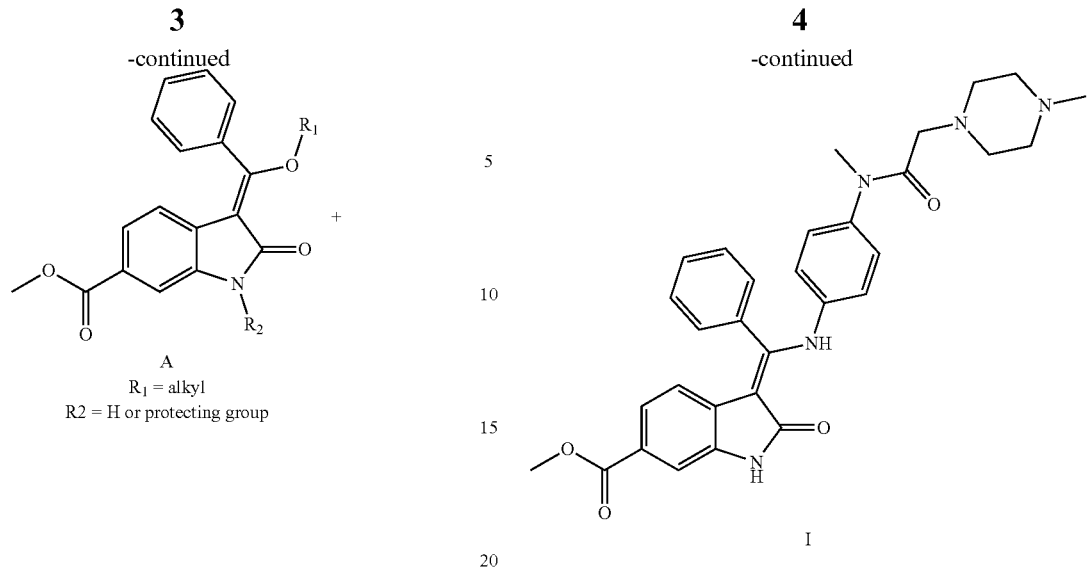

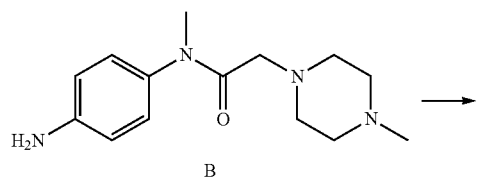

Another synthetic method is reported in patent CN104262232A. As shown in the following procedure, the condensation of two fragments is firstly carried out in the method, and then the reduction and cyclization reactions are carried out. But the condensation reaction of the process requires high temperature and the yield of the substitution reaction is low, thus the synthetic method is not suitable for industrial scale-up.

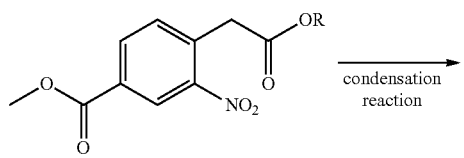

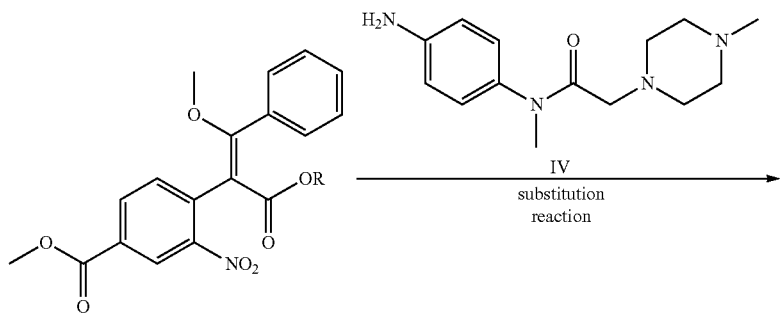

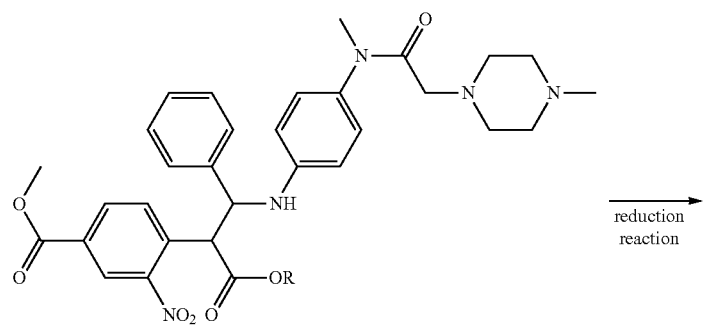

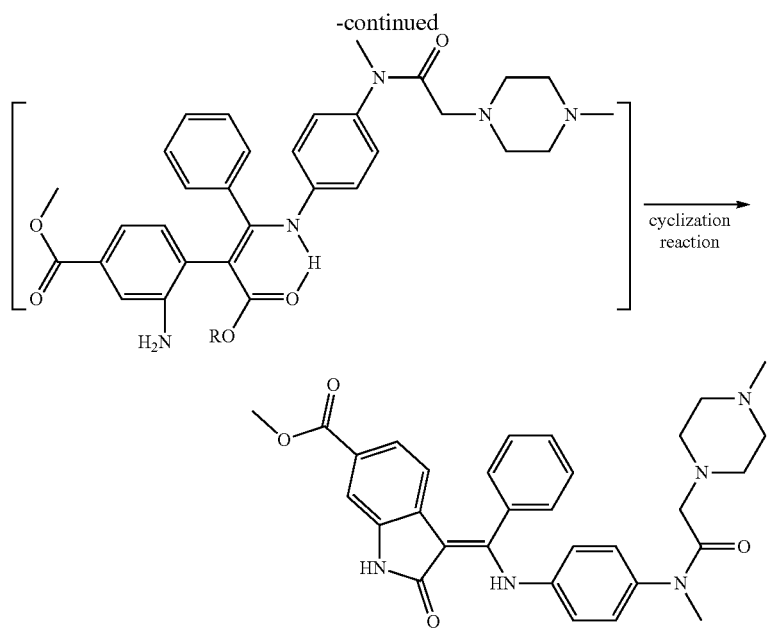

In summary, there are few preparation routes feasible for Nintedanib currently, and the costs thereof are high. So the development of synthetic routes with simple process, mild conditions and high yield can greatly improve their preparation efficiency, reduce cost, decrease pollution and improve social and economic benefits.

SUMMARY

The present application relates to a novel preparation method of Nindedanib (I), and key intermediates i.e. methyl 4-(1-methoxy-1,3-dioxo-3-phenylpropan-2-yl)-3-nitrobenzoate (formula IV) and methyl 3-benzoyl-2-oxoindoline-6-formate (formula V) involved in the method, and preparation methods of the above key intermediates, to solve the problems existed in the prior art.

In a first aspect, the preparation process of the preparation method of nintedanib of the present application is as follows:

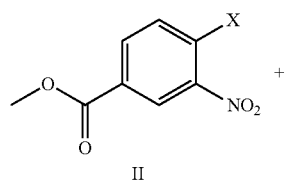

II

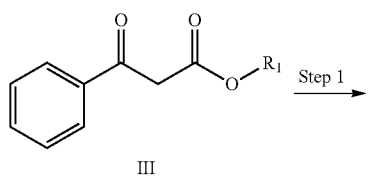

III

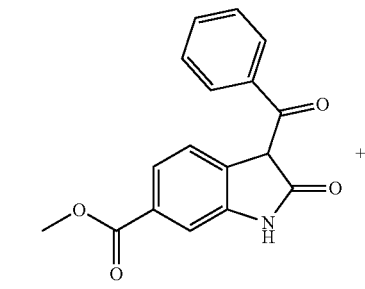

IV

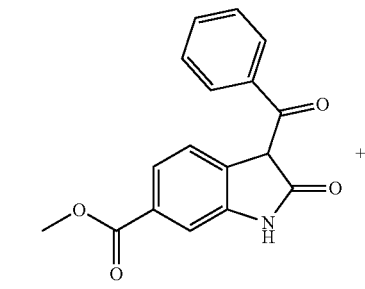

V

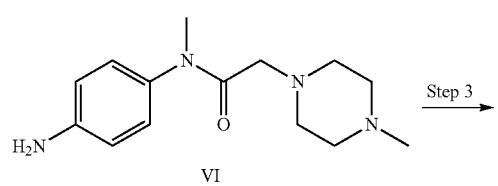

VI

-continued

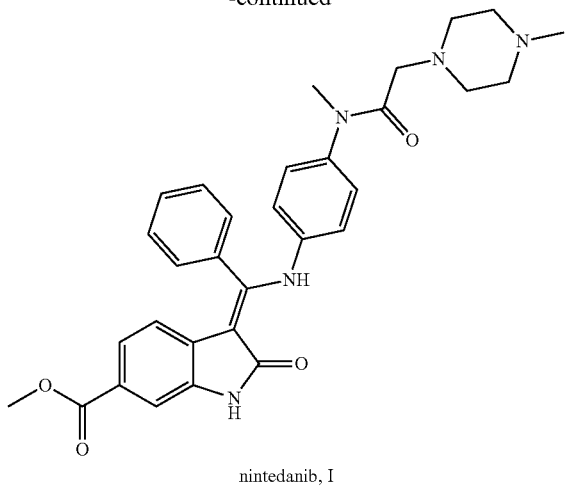

nintedanib, I

That is, the preparation method of nintedanib includes the following steps:

Step 1: reacting compound II, i.e. methyl 4-halo-3-nitrobenzoate with compound III, i.e. 3-oxo-3-phenylpropionate under the action of a base to form compound IV, i.e. methyl 4-(1-alkoxy-1,3-dioxo-3-phenylpropan-2-yl)-3-nitrobenzoate;

wherein, X is a halogen, preferably chlorine or bromine in compound II; $R_1$ is an alkyl or a substituted alkyl, preferably a C1-C6 alkyl or C7-C12 aromatic alkyl, more preferably methyl or ethyl in compounds III and IV; the base is NaH, sodium methoxide, potassium tert-butoxide, lithium tert-butoxide, sodium hydroxide, potassium hydroxide, potassium carbonate or sodium carbonate; the solvent for the reaction is N,N-dimethylformamide, N,N-dimethylacetamide, N-methylpyrrolidone, 1,4-dioxane, 1,2-dichloroethane or acetonitrile; the temperature of the reaction in step 1 is 50-120° C., preferably 60-90° C.;

Step 2: subjecting the above compound IV to a reduction-cyclization reaction in a suitable reducing reagent and a suitable solvent to form compound V, i.e. methyl 3-benzoyl-2-oxoindoline-6-formate;

wherein, the reducing reagent is preferably hydrogen, palladium-carbon, platinum carbon, palladium hydroxide, Raney nickel, iron powder, zinc powder, tin powder, aluminum powder, hydrazine hydrate, sodium hydrosulfite, stannous chloride, sodium sulfide or formic acid-triethylamine; the solvent is preferably methanol, ethanol, ethyl acetate, acetic acid or N,N-dimethylformamide; the temperature of the reaction is 50-120° C., preferably 70-100° C.;

Step 3: reacting the above compound V with raw material compound VI, i.e. N-(4-aminophenyl)-N-methyl-2-(4-methylpiperazin-1-yl)acetamide in the action of an acid and a suitable solvent to form compound I, i.e., nintedanib;

wherein the acid is preferably formic acid, acetic acid, trifluoroacetic acid, methanesulfonic acid, trifluoromethanesulfonic acid or p-toluenesulfonic acid; the solvent is preferably toluene, xylene, N,N-dimethylformamide, N,N-dimethylacetamide, N-methylpyrrolidone or 1,4-dioxane; the temperature of the reaction in step 3 is 60-120° C., preferably 80-110° C.

Alternatively, the preparation process is as follows:

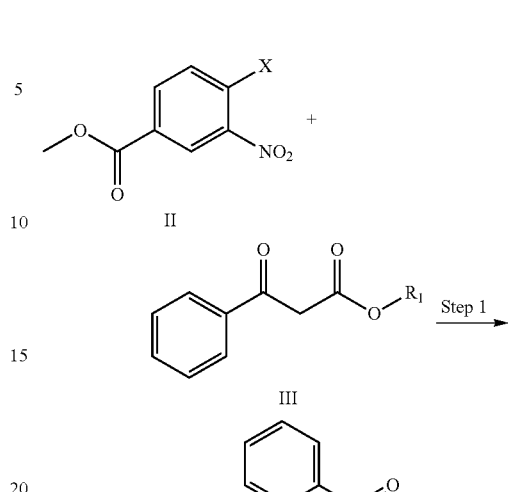

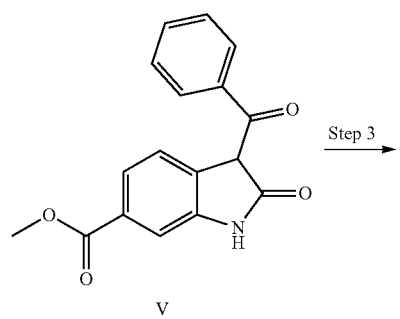

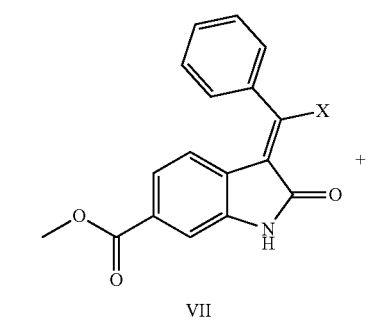

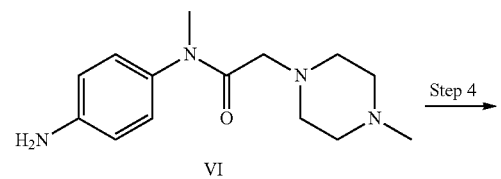

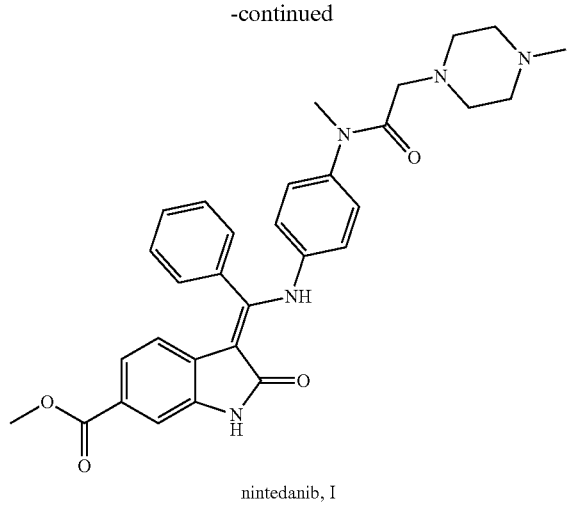

nintedanib, I

That is, the preparation method of nintedanib includes the following steps:

Step 1: reacting compound II, i.e. methyl 4-halo-3-nitrobenzoate with compound III, i.e. 3-oxo-3-phenylpropionate under the action of a base to form compound IV, i.e. methyl 4-(1-alkoxy-1,3-dioxo-3-phenylpropan-2-yl)-3-nitrobenzoate;

wherein, X is a halogen, preferably chlorine or bromine; $R_1$ is an alkyl or a substituted alkyl, preferably a C1-C6 alkyl or C7-C12 aromatic alkyl, more preferably methyl or ethyl; the base is preferably sodium methoxide, potassium tert-butoxide, sodium hydroxide, potassium hydroxide or potassium carbonate; the solvent is preferably N,N-dimethylformamide, N,N-dimethylacetamide, N-methylpyrrolidone, 1,4-dioxane or acetonitrile; the temperature of the reaction in step 1 is 50-120° C., preferably 60-90° C.;

Step 2: subjecting the above compound IV to a reduction-cyclization reaction in a suitable reducing reagent and a suitable solvent to form compound V, i.e. methyl 3-benzoyl-2-oxoindoline-6-formate;

wherein the reducing agent is preferably hydrogen, palladium-carbon, platinum carbon, Raney nickel, iron powder, zinc powder, hydrazine hydrate or sodium dithionite; the solvent is preferably methanol, ethanol, ethyl acetate or acetic acid; the temperature of the reaction is 20-120° C., preferably 20-80° C.;

Step 3: reacting the above compound V in a halogenating reagent, a base or a catalyst and a suitable solvent to form an intermediate compound VII, i.e. methyl (Z,E)-(3-halo-3-phenylmethylene)-2-oxoindoline-6-formate;

wherein, X is a halogen, preferably chlorine or bromine; the halogenating reagent is preferably phosphorus oxychloride, phosphorus tribromide or phosphorus pentachloride; the base is preferably triethylamine, diisopropylethylamine, DBU, dimethylaminopyridine or N,N-dimethylformamide; the solvent is preferably toluene, acetonitrile, dioxane or phosphorus oxychloride; the temperature of the reaction is 50-120° C., preferably 60-100° C.;

Step 4: reacting the above intermediate compound VII with compound VI under a base and a suitable solvent to form compound I, i.e. nintedanib;

wherein, the base is preferably triethylamine, diisopropylethylamine, sodium bicarbonate, sodium carbonate or potassium carbonate; the solvent is preferably methanol, ethanol, acetonitrile, N,N-dimethylformamide or 1,4-dioxane; the temperature of the reaction is 20-80° C., preferably 50-70° C.

Preferably, the next reaction step can be directly carried out without separation in the process of forming compound VII from compound V; the specific reaction formula is as follows:

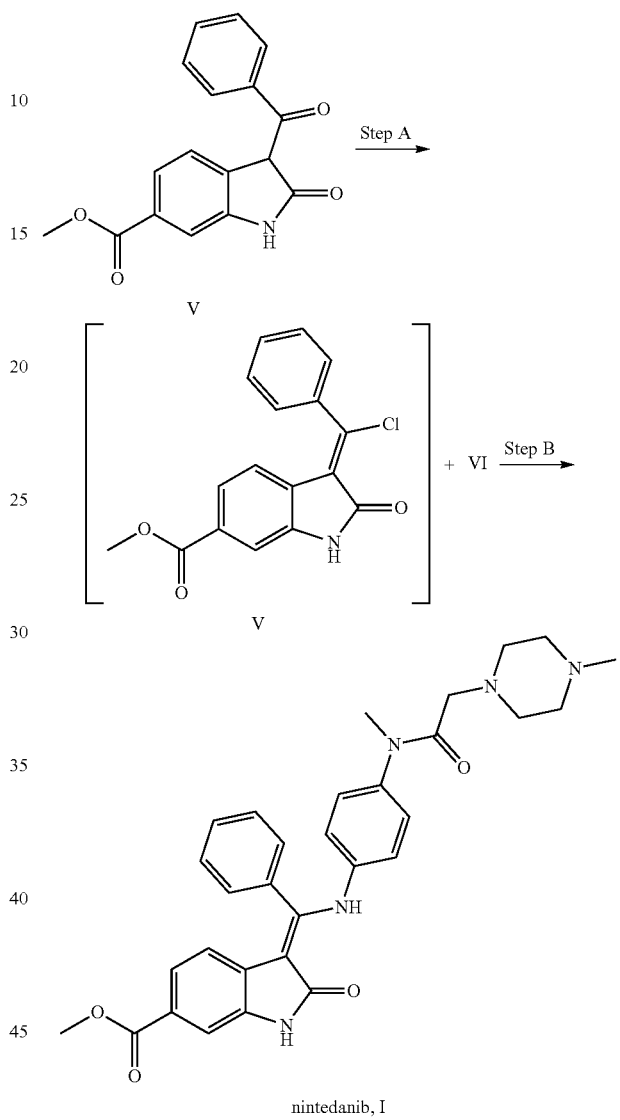

nintedanib, I wherein, Step A: forming compound VII from compound V in a halogenating agent and a base;

Step B: adding compound VI and a base directly to the system after the reaction of the step A without separation, and reacting to form nintedanib;

wherein, the step A is carried out without solvent or in an organic solvent selected from toluene, acetonitrile or dioxane; the halogenating agent is selected from phosphorus oxychloride, phosphorus pentoxide or phosphorus pentachloride, preferably phosphorus oxychloride; the base is selected from triethylamine, diisopropylethylamine or DBU, preferably diisopropylethylamine;

the step B is carried out in a solvent selected from methanol, ethanol, acetonitrile, tetrahydrofuran or dichloromethane, or a mixed solvent thereof; and the base used is selected from triethylamine, diisopropylethylamine, sodium bicarbonate, sodium carbonate or potassium carbonate.

In another aspect, the present application also provides novel compounds IV, V and compound VII having the structural formulas as follow:

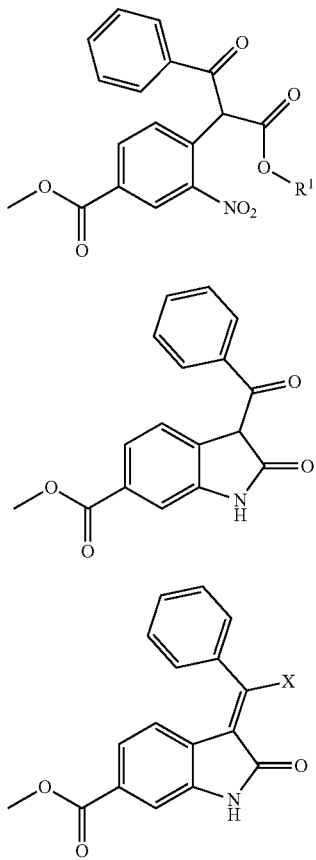

wherein, $R_1$ is alkyl or substituted alkyl, preferably C1-C6 alkyl or C7-12 aromatic alkyl, more preferably methyl or ethyl; X is a halogen, preferably chlorine or bromine.

The compounds IV, V or VII provided by the present application can be used for the preparation of the drug of nintedanib. The use of the above new intermediate compounds shortens the reaction steps and avoids the use of dangerous chemical raw materials. The final product of nintedanib obtained has good quality and high purity, and is suitable for industrial production.

Accordingly, the present application provides the use of Compounds IV, V or VII for the preparation of a drug of nintedanib.

The configuration of the nintedanib (I) obtained by the method of the present application has specificity, and only the Z-isomer can be obtained without the impurity of E-configuration, and the product has good purity and has the advantage of product stability.

Compared with the prior art, the preparation method of nintedanib (1) provided by the present application has the advantages that raw materials are easily obtainable, processes are simple, operation steps are shortened, the operation process is simplified, the production efficiency is improved; in addition, each step thereof is easy to be purified, with high yield, safe and environmentally friendly and suitable for industrial production.

EMBODIMENT

The technical solutions of the present application are specifically described below without limitation by way of specific embodiments. Wherein raw materials II and III can be purchased in bulk; raw material VI can be synthesized by the method of J. Med. Chem, 2009, 52, 4466-4480 or patent WO2009071523.

Example 1: Preparation of Methyl 4-(1-methoxy-1, 3-dioxo-3-phenylpropan-2-yl)-3-nitrobenzoate (IV)

Into a 500 mL reaction flask, 160 mL of N,N-dimethyl-formamide and 18.8 g of methyl 4-chloro-3-nitro-benzoate were added, stirred until fully dissolved at 25° C. Then 17.1 g of 3-oxo-3-phenylpropionate and 24.1 g of anhydrous potassium carbonate were added successively, heated to 80-90° C. to start the reaction, reacted for 4-6 hours until TLC showed the disappearance of the raw materials. Glacial acetic acid was added to the reaction solution to adjust the pH to neutrality, and 600 mL of water was added thereto, followed by extraction with ethyl acetate (200 mL*3 times). The ethyl acetate layers were combined and washed with 5% NaCl solution (300 mL*2 times). The ethyl acetate layer was dried over anhydrous magnesium sulfate and then the solvent was rotarily evaporated to dryness to obtain 28.7 g of compound IV, yield 92.1%. $^1$H NMR (400 MHz, CDCl$_3$): δ 8.38-8.33 (m, 2H), 7.98-7.93 (m, 2H), 7.79 (d, J=7.6, 1H), 7.64-7.56 (m, 1H), 7.50 (m, 2H), 5.16 (d, J=0.9 Hz, 1H), 3.95 (s, 3H), 3.75 (s, 3H).
Mass: 358.0 [M+H$^+$].

Example 2: Preparation of Nintedanib (I)

Into a 500 mL reaction flask, 21.2 g of compound V was dissolved in 210 mL of toluene, 20.7 g of compound IV and 2.47 g of p-toluenesulfonic acid were added, heated to 100-110° C., refluxed and reacted, the resulting water was separated by Dean-Stark. TLC showed complete conversion of the raw materials after 28 hours of reaction. Cooled to room temperature, then washed once with 5% NaHCO$_3$ solution, twice with 5% NaCl solution, and dried over 10 g of anhydrous magnesium sulfate. The toluene was evaporated to dryness, and then recrystallized by adding 120 mL of methanol/n-heptane to obtain 24.7 g of the product nintedanib, yield 63.8%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, J=7.6 Hz, 1H), 7.43-7.40 (d, J=1.6 Hz, 1H), 7.21-7.17 (d, J=8.3 Hz, 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

Example 3: Preparation of Methyl 4-(1-ethoxy-1,3-dioxo-3-phenylpropan-2-yl)-3-nitrobenzoate (IV)

Into a 250 mL reaction flask, 120 mL of N,N-dimethyl-acetamide and 12.0 g of methyl 4-bromo-3-nitro-benzoate were added, stirred until fully dissolved at 25° C. Then 15.3 g of ethyl 3-oxo-3-phenylpropionate and 7.7 g of sodium methoxide were added successively, heated to 80-90° C. to start the reaction and reacted for 4-6 hours until TLC showed the disappearance of the raw materials. Glacial acetic acid was added to the reaction solution to adjust the pH to neutrality, 300 mL of water was added, then extracted with ethyl acetate (100 mL*3 times). The ethyl acetate layers were combined and washed with 5% NaCl solution (200 mL*2 times). The ethyl acetate layer was dried over anhydrous magnesium sulfate and then the solvent was rotarily evaporated to dryness to obtain 15.3 g of compound IV, yield 89.3%. ¹H-NMR (500 MHz, Chloroform-d) δ 8.36 (s, 1H), 8.38-8.32 (m, 1H), 7.80 (ddd, J=16.0, 7.3, 1.6 Hz, 3H), 7.64-7.56 (m, 1H), 7.50 (t, J=7.4 Hz, 2H), 5.05 (d, J=1.1 Hz, 1H), 4.53 (dq, J=12.5, 8.0 Hz, 1H), 3.95 (s, 3H), 3.77 (dq, J=12.5, 8.0 Hz, 1H), 1.22 (t, J=8.0 Hz, 3H). Mass: 371.3 [M+H⁺].

Example 4: Preparation of Methyl 4-(1-methoxy-1, 3-dioxo-3-phenylpropan-2-yl)-3-nitrobenzoate (IV)

Into a 250 mL reaction flask, 120 mL of N-methylpyrrolidone and 12.0 g of methyl 4-chloro-3-nitro-benzoate were added, stirred until fully dissolved at 25° C. Then 10.9 g of methyl 3-oxo-3-phenylpropionate and 7.5 g of potassium tert-butoxide were added successively, heated to 80-90° C. to start the reaction and reacted for 2-3 hours until TLC showed the disappearance of the raw materials. Glacial acetic acid was added to the reaction solution to adjust the pH to neutrality, 300 mL of water was added, and then extracted with ethyl acetate (100 mL*3 times). The ethyl acetate layers were combined and washed with 5% NaCl solution (200 mL*2 times). The ethyl acetate layer was dried over anhydrous magnesium sulfate and then the solvent was rotarily evaporated to dryness to obtain 17.9 g of compound IV, yield 90.0%. ¹H NMR (400 MHz, CDCl₃): δ 8.38-8.33 (m, 2H), 7.98-7.93 (m, 2H), 7.79 (d, J=7.6, 1H), 7.64-7.56 (m, 1H), 7.50 (m, 2H), 5.16 (d, J=0.9 Hz, 1H), 3.95 (s, 3H), 3.75 (s, 3H). Mass: 358.3 [M+H⁺].

Example 5: Preparation of Methyl 4-(1-methoxy-1, 3-dioxo-3-phenylpropan-2-yl)-3-nitrobenzoate (IV)

Into a 250 mL reaction flask, 120 mL of 1,4-dioxane and 12.0 g of methyl 4-chloro-3-nitro-benzoate were added, stirred until fully dissolved at 25° C. Then 10.9 g of ethyl 3-oxo-3-phenylpropionate and 4.7 g of potassium hydroxide were added successively, heated to 80-90° C. to start the reaction and reacted for 2-3 hours until TLC showed the disappearance of the raw materials. Glacial acetic acid was added to the reaction solution to adjust the pH to neutrality, 300 mL of water was added, and then extracted with ethyl acetate (100 mL*3 times). The ethyl acetate layers were combined and washed with 5% NaCl solution (200 mL*2 times). The ethyl acetate layer was dried over anhydrous magnesium sulfate and then the solvent was rotarily evaporated to dryness to obtain 18.0 g of compound IV, yield 90.5%. ¹H NMR (400 MHz, CDCl₃): δ 8.38-8.33 (m, 2H), 7.98-7.93 (m, 2H), 7.79 (d, J=7.6, 1H), 7.64-7.56 (m, 1H), 7.50 (m, 2H), 5.16 (d, J=0.9 Hz; 1H), 3.95 (s, 3H), 3.75 (s, 3H). Mass: 358.3 [M+H⁺].

Example 6: Preparation of Methyl 4-(1-methoxy-1, 3-dioxo-3-phenylpropan-2-yl)-3-nitrobenzoate (IV)

Into a 250 mL reaction flask, 120 mL of acetonitrile and 12.0 g of methyl 4-chloro-3-nitro-benzoate were added, stirred until fully dissolved at 25° C. Then, 10.9 g of ethyl 3-oxo-3-phenylpropionate and 3.3 g of sodium hydroxide were added successively, heated to 80-90° C. to start the reaction and reacted for 2-3 hours until TLC showed the disappearance of the raw materials. Glacial acetic acid was added to the reaction solution to adjust the pH to neutrality, 300 mL of water was added, and then extracted with ethyl acetate (100 mL*3 times). The ethyl acetate layers were combined and washed with 5% NaCl solution (200 mL*2 times). The ethyl acetate layer was dried over anhydrous magnesium sulfate and then the solvent was rotarily evaporated to dryness to obtain 18.4 g of compound IV, yield 92.5%. ¹H NMR (400 MHz, CDCl₃): δ 8.38-8.33 (m, 2H), 7.98-7.93 (m, 2H), 7.79 (d, J=7.6, 1H), 7.64-7.56 (m, 1H), 7.50 (m, 2H), 5.16 (d, J=0.9 Hz, 1H), 3.95 (s, 3H), 3.75 (s, 3H). Mass: 358.3 [M+H⁺].

Example 7: Preparation of Methyl 3-benzoyl-2-oxoindoline-6-formate (V)

Into a 500 mL reaction flask, 24.0 g of compound IV was dissolved in 240 mL of ethyl acetate, 2.4 g of 10% palladium-carbon catalyst was added, and reacted under 3 atmospheres of hydrogen at 20-30° C. for 16 hours until TLC showed the raw materials are completely converted to form an intermediate. Then heated to 70-80° C., reacted for 4-6 hours until TLC showed complete conversion of the intermediate. Cooled to room temperature, the palladium-carbon catalyst was filtered off, the ethyl acetate solution was evaporated to dryness and replaced with methyl tert-butyl ether, the product was recrystallized to obtain 16.2 g of white crystal, yield 81.7%. ¹H NMR (400 MHz, CDCl₃) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H⁺].

Example 8: Preparation of Methyl 3-benzoyl-2-oxoindoline-6-formate (V)

Into a 100 mL reaction flask, 5.0 g of compound IV was dissolved in 50 mL of methanol, 0.5 g of 10% platinum-carbon catalyst was added, and reacted under 8 atmospheres of hydrogen at 20-30° C. for 4 hours until TLC showed the raw materials are completely converted to form an intermediate. Then heated to 60-70° C., reacted for 2 hours until TLC showed complete conversion of the intermediate. Cooled to room temperature, the platinum-carbon catalyst was filtered off, the ethyl acetate solution was evaporated to dryness and replaced with methyl tert-butyl ether, the product was recrystallized to obtain 3.6 g of white crystal, yield 87.1%. ¹H NMR (400 MHz, CDCl₃) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H⁺].

Example 9: Preparation of Methyl 3-benzoyl-2-oxoindoline-6-formate (V)

Into a 100 mL reaction flask, 5.0 g of compound IV was dissolved in 50 mL of acetic acid, 3.1 g of iron powder was added, heated to 60-70° C., reacted for 20 hours until complete conversion. Cooled to room temperature, the iron powder was filtered off, the acetic acid was evaporated to dryness, extracted with ethyl acetate/saturated sodium bicarbonate to obtain an organic layer, replaced ethyl acetate with methyl tert-butyl ether and the product was recrystallized to obtain 2.9 g of white crystal, yield 70.2%. ¹H NMR (400 MHz, CDCl₃) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H⁺].

Example 10: Preparation of Methyl 3-benzoyl-2-oxoindoline-6-formate (V)

Into a 100 mL reaction flask, 5.0 g of compound IV was dissolved in 50 mL of methanol, 0.5 g of 10% Raney nickel catalyst was added, and reacted under 5 atmospheres of hydrogen at 20-30° C. for 1 hour until TLC showed the raw materials are completely converted to form an intermediate. Then heated to 60-70° C., reacted for 1 hour until TLC showed complete conversion of the intermediate. Cooled to room temperature, the catalyst was filtered off, the ethyl acetate solution was evaporated to dryness and replaced with methyl tert-butyl ether, the product was recrystallized to obtain 3.2 g of white crystal, yield 77.4%. $^1$H NMR (400 MHz, CDCl$_3$) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.0 [M+H$^+$].

Example 11: Preparation of Methyl 3-benzoyl-2-oxoindoline-6-formate (V)

Into a 100 mL reaction flask, 5.0 g of compound IV was dissolved in 50 mL of acetic acid, 3.6 g of zinc powder was added, heated to 60-70° C., reacted for 48 hours until complete conversion. Cooled to room temperature, the zinc powder was filtered off, the acetic acid was evaporated to dryness, extracted with ethyl acetate/saturated sodium bicarbonate to obtain an organic layer, replaced ethyl acetate with methyl tert-butyl ether and the product was recrystallized to obtain 3.1 g of white crystal, yield 75.2%. $^1$H NMR (400 MHz, CDCl$_3$) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H$^+$].

Example 12: Preparation of Methyl 3-benzoyl-2-oxoindoline-6-formate (V)

Into a 100 mL reaction flask, 5.0 g of compound IV was dissolved in 50 mL of methanol, 0.5 g of 10% palladium-carbon catalyst powder and 2.0 eq hydrazine hydrate were added, heated to 60-70° C., reacted for 20 hours until complete conversion. Cooled to room temperature, the catalyst was filtered off, the methanol was evaporated to dryness, extracted with ethyl acetate/1N diluted hydrochloric acid to obtain an organic layer, replaced ethyl acetate with methyl tert-butyl ether and the product was recrystallized to obtain 2.8 g of white crystal, yield 67.8%. $^1$H NMR (400 MHz, CDCl$_3$) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H$^+$].

Example 13: Preparation of Methyl 3-benzoyl-2-oxoindoline-6-formate (V)

Into a 100 mL reaction flask, 5.0 g of compound IV was dissolved in 50 mL of methanol, 9.8 g of sodium hydrosulfite was added, heated to 60-70° C. reacted for 40 hours until complete conversion. Cooled to room temperature, the methanol was evaporated to dryness, extracted with ethyl acetate/1N diluted hydrochloric acid to obtain an organic layer, replaced ethyl acetate with methyl tert-butyl ether and the product was recrystallized to obtain 3.3 g of white crystal, yield 79.9%. $^1$H NMR (400 MHz, CDCl$_3$) δ 8.55 (br, 1H), 8.13 (s, 1H), 8.09-8.01 (m, 2H), 7.88 (dd, J=7.6, 1.6 Hz, 1H), 7.76-7.65 (m, 2H), 7.52-7.40 (m, 2H), 5.33 (s, 1H), 3.87 (s, 3H). Mass: 296.3 [M+H$^+$].

Example 14: Preparation of Methyl (3-chloro-3-phenylmethylene)-2-oxoindoline-6-formate (VII)

Into a 500 mL reaction flask, 33.1 g of compound V was dissolved in 132 mL of phosphorus oxychloride and 66 mL of diisopropylethylamine, heated to 60-80° C. under the protection of nitrogen atmosphere and reacted for 1-2 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dt, J=4.1, 1.8 Hz, 2H), 7.42-7.31 (m, 4H), 7.11 (tt, J=7.2, 2.3 Hz, 1H), 6.95 (d, J=7.9 Hz, 1H), 3.95 (s, 3H). Mass: 314.0 [M+H$^+$]. Used directly in the next step.

Example 15: Preparation of Methyl (3-chloro-3-phenylmethylene)-2-oxoindoline-6-formate (VII)

Into a 500 mL reaction flask, 33.1 g of compound V was dissolved in 132 mL of phosphorus oxychloride and 66 mL of triethylamine, heated to 80-100° C. under the protection of nitrogen atmosphere and reacted for 1-2 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dt, J=4.1, 1.8 Hz, 2H), 7.42-7.31 (m, 4H), 7.11 (tt, J=7.2, 2.3 Hz, 1H), 6.95 (d, J=7.9 Hz, 1H), 3.95 (s, 3H). Mass: 314.0 [M+H$^+$]. Used directly in the next step.

Example 16: Preparation of Methyl (3-bromo-3-phenylmethylene)-2-oxoindoline-6-formate (VII)

Into a 500 mL reaction flask, 33.1 g of compound V was dissolved in 99 mL of acetonitrile, 27.3 g of phosphorus tribromide and 66 mL of triethylamine were added, heated to 60-80° C. under the protection of nitrogen atmosphere and reacted for 3-4 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dq, J=2.8, 1.6 Hz, 2H), 7.42-7.34 (m, 2H), 7.35-7.28 (m, 2H), 7.11 (tt, J=7.3, 2.1 Hz, 1H), 6.98 (d, J=7.9 Hz, 1H), 3.95 (s, 3H). Mass: 358.0 [M+H$^+$]. Used directly in the next step.

Example 17: Preparation of Methyl (3-bromo-3-phenylmethylene)-2-oxoindoline-6-formate (VII)

Into a 500 mL reaction flask, 33.1 g of compound V was dissolved in 99 mL of dioxane, 27.3 g of phosphorus tribromide and 66 mL of DBU were added, heated to 80-100° C. under the protection of nitrogen atmosphere and reacted for 1-2 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dq, J=2.8, 1.6 Hz, 2H), 7.42-7.34 (m, 2H), 7.35-7.28 (m, 2H), 7.11 (tt, J=7.3, 2.1 Hz, 1H), 6.98 (d, J=7.9 Hz, 1H), 3.95 (s, 3H). Mass: 358.0 [M+H$^+$]. Mass: 358.0 [M+H$^+$]. Used directly in the next step.

Example 18: Preparation of Methyl (3-chloro-3-phenylmethylene)-2-oxoindoline-6-formate (VII)

Into a 500 mL reaction flask, 10.2 g of compound V was dissolved in 41 mL of phosphorus oxychloride and 2 mL of dimethylaminopyridine, heated to 60-80° C. under the protection of nitrogen atmosphere and reacted for 1-2 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dt, J=4.1, 1.8 Hz, 2H), 7.42-7.31 (m, 4H), 7.11 (tt, J=7.2, 2.3 Hz, 1H), 6.95 (d, J=7.9 Hz, 1H), 3.95 (s, 3H). Mass: 314.0 [M+H$^+$]. Used directly in the next step.

Example 19: Preparation of Methyl (3-chloro-3-phenylmethylene)-2-oxoindoline-6-formate (VII)

Into a 500 mL reaction flask, 10.2 g of compound V was dissolved in 41 mL of phosphorus oxychloride and 2 mL of N,N-dimethylformamide, heated to 60-80° C. under the protection of nitrogen atmosphere and reacted for 1-2 hours. After the TLC showed the complete conversion of the raw materials, the solvent was evaporated to dryness, extracted with ethyl acetate/water to obtain an organic phase, evaporated to dryness to obtain a brown oily intermediate VII. $^1$H NMR (500 MHz, Chloroform-d) δ 8.59 (s, 1H), 7.73 (dt, J=4.1, 1.8 Hz, 2H), 7.42-7.31 (m, 4H), 7.11 (tt, J=7.2, 2.3 Hz, 1H), 6.95 (d, J=7.9 Hz, 1H), 3.95 (s, 3H). Mass: 314.0 [M+H$^+$]. Used directly in the next step.

Example 20: Preparation of Nintedanib (I)

Into a 500 mL reaction flask, 200 mL of ethanol was added to 25.0 g of methyl (3-chloro-3-phenylmethylene)-2-oxoindoline-6-formate oil which was obtained by rotary evaporation from the previous reaction step, stirred until fully dissolved, 20.9 g of compound VI and 12.1 g of triethylamine were added, heated to 60-70° C. and reacted for 6 hours until TLC showed the disappearance of the raw materials. The reaction solution was evaporated to dryness and replaced with 200 mL of ethyl acetate, washed with water (100 mL*3 times), and then 6.6 g of anhydrous magnesium sulfate was added for drying and 6.6 g of activated carbon was added for decolorization successively. The obtained solution was evaporated to dryness and replaced with methanol/n-heptane, crystallized to obtain 36.8 g of nintedanib, yield 85.6%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, J=7.6 Hz, 1H), 7.43-7.40 (d, J=1.6 Hz, 1H), 7.21-7.17 (d, J=8.3 Hz, 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

Example 21: Preparation of Nintedanib (I)

Into a 500 mL reaction flask, 200 mL of methanol was added to 25.0 g of methyl (3-chloro-3-phenylmethylene)-2-oxoindoline-6-formate oil which was obtained by rotary evaporation from the previous reaction step, stirred until fully dissolved, 20.9 g of compound VI and 15.5 g of diisopropylethylamine were added, heated to 50-60° C. and reacted for 10 hours until TLC showed the disappearance of the raw materials. The reaction solution was evaporated to dryness and replaced with 200 mL of ethyl acetate, washed with water (100 mL*3 times), and then 6.6 g of anhydrous magnesium sulfate was added for drying and 6.6 g of activated carbon was added for decolorization successively. The obtained solution was evaporated to dryness and replaced with methanol/n-heptane, crystallized to obtain 37.1 g of nintedanib, yield 86.1%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, J=7.6 Hz, 1H), 7.43-7.40 (d, J=1.6 Hz, 1H), 7.21-7.17 (d, J=8.3 Hz, 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

Example 22: Preparation of Nintedanib (I)

Into a 500 mL reaction flask, 200 mL of acetonitrile was added to 25.0 g of methyl (3-chloro-3-phenylmethylene)-2-oxoindoline-6-formate oil which was obtained by rotary evaporation from the previous reaction step, stirred until fully dissolved, 20.9 g of compound VI and 10.1 g of sodium bicarbonate were added, heated to 60-70° C. and reacted for 16 hours until TLC showed the disappearance of the raw materials. After filtered to remove the salt, the reaction solution was evaporated to dryness and replaced with 200 mL of ethyl acetate, washed with water (100 mL*3 times), and then 6.6 g of anhydrous magnesium sulfate was added for drying and 6.6 g of activated carbon was added for decolorization successively. The obtained solution was evaporated to dryness and replaced with methanol/n-heptane, crystallized to obtain 35.9 g of nintedanib, yield 83.5%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, J=7.6 Hz, 1H), 7.43-7.40 (d, J=1.6 Hz, 1H), 7.21-7.17 (d, J=8.3 Hz, 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

Example 23: Preparation of Nintedanib (I)

Into a 500 mL reaction flask, 200 mL of N,N-dimethylformamide was added to 25.0 g of methyl (3-chloro-3-phenylmethylene)-2-oxoindoline-6-formate oil which was obtained by rotary evaporation from the previous reaction step, stirred until fully dissolved, 20.9 g of compound VI and 12.7 g of sodium carbonate were added, heated to 60-70° C. and reacted for 5-6 hours until TLC showed the disappearance of the raw materials. After filtered to remove the salt, the reaction solution was evaporated to dryness and replaced with 200 mL of ethyl acetate, washed with water (100 mL*3 times), and then 6.6 g of anhydrous magnesium sulfate was added for drying and 6.6 g of activated carbon was added for decolorization successively. The obtained to solution was evaporated to dryness and replaced with methanol/n-heptane, crystallized to obtain 34.5 g of nintedanib, yield 80.2%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, J=7.6 Hz, 1H), 7.43-7.40 (d, J=1.6 Hz, 1H), 7.21-7.17 (d, 0.1=8.3 Hz; 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

Example 24: Preparation of Nintedanib (I)

Into a 500 mL reaction flask, 150 mL of 1,4-dioxane was added to 25.0 g of methyl (3-bromo-3-phenylmethylene)-2-oxoindoline-6-formate oil which was obtained by rotary evaporation from the previous reaction step, stirred until fully dissolved, 13.2 g of compound VI and 10.4 g of potassium carbonate were added, heated to 50-60° C. and reacted for 1-2 hours until TLC showed the disappearance of the raw materials. After filtered to remove the salt, the reaction solution was evaporated to dryness and replaced with 200 mL of ethyl acetate, washed with water (100 mL*3 times), and then 6.6 g of anhydrous magnesium sulfate was added for drying and 6.6 g of activated carbon was added for decolorization successively. The obtained solution was evaporated to dryness and replaced with methanol/n-heptane, crystallized to obtain 22.2 g of nintedanib, yield 81.9%. $^1$H NMR (400 MHz, DMSO-d$_6$): 12.17 (s, 1H), 11.03 (s, 1H), 7.64-7.59 (t, J=7.6 Hz, 2H), 7.56-7.52 (t, J=7.6 Hz, 2H), 7.50-7.45 (d, 0.1=7.6 Hz, 1H), 7.43-7.40 (d, J=1.6 Hz, 1H), 7.21-7.17 (d J=8.3 Hz, 1H), 7.15-7.07 (m, 2H), 6.82-6.77 (m, 2H), 5.85-5.83 (d, J=8.3 Hz, 1H), 3.79 (s, 3H), 3.11-3.04 (m, 3H), 2.75-2.66 (m, 2H), 2.27-2.19 (m, 5H), 2.16-2.11 (m, 3H), 2.10 (s, 3H). Mass: 540.2 [M+H$^+$].

The invention claimed is:

1. A preparation method of nintedanib, comprising the following preparation processes:

preparation process 1

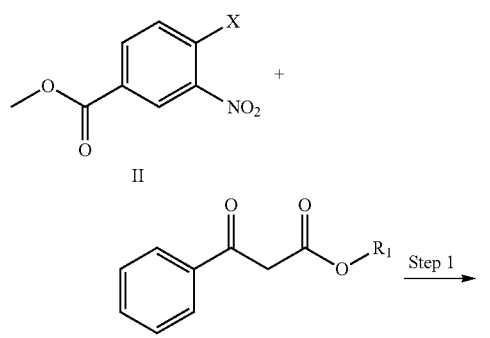

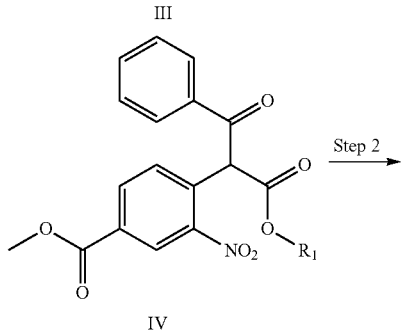

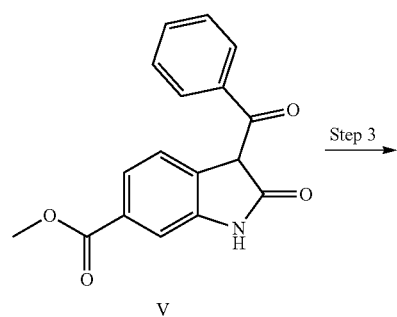

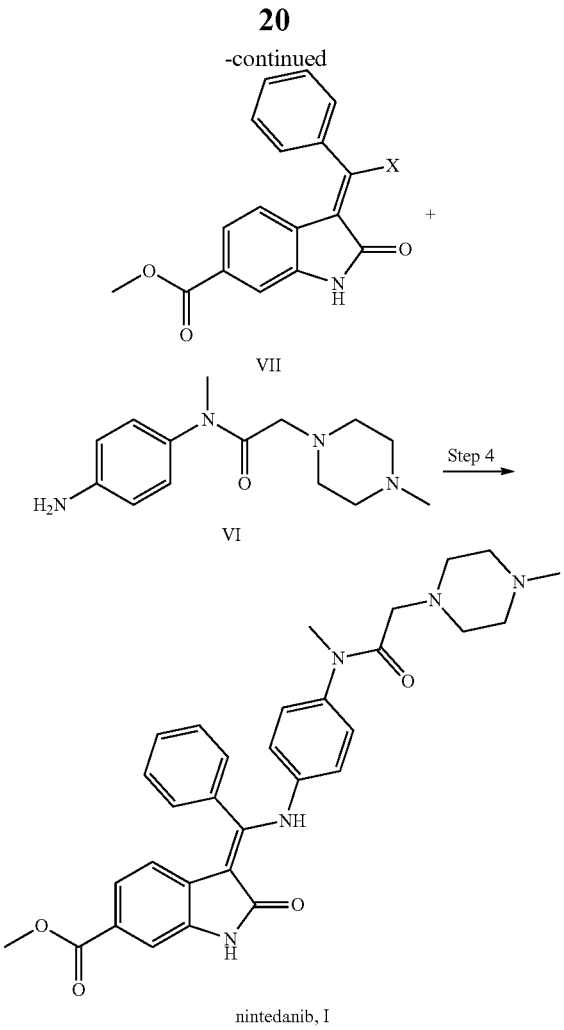

nintedanib, I wherein,

Step 1: reacting compound II with compound III under the action of a base to form compound IV;

wherein, X is a halogen in the compound II; R$_1$ is an alkyl or a C7-C12 aromatic alkyl in compounds III and IV; the base is selected from sodium methoxide, potassium tert-butoxide, sodium hydroxide, potassium hydroxide or potassium carbonate; the solvent is selected from N,N-dimethylformamide, N,N-dimethylacetamide, N-methylpyrrolidone, 1,4-dioxane or acetonitrile; the temperature of the reaction in step 1 is 50-120° C.;

Step 2: subjecting compound IV to a reduction-cyclization reaction in a reducing reagent and a solvent to form compound V;

wherein the reducing agent is hydrogen, palladium-carbon, platinum carbon, Raney nickel, iron powder, zinc powder, hydrazine hydrate or sodium dithionite; the solvent is selected from methanol, ethanol, ethyl acetate or acetic acid; the temperature of the reaction is 20-120° C.;

Step 3: reacting the above compound V in a halogenating reagent, a base or a catalyst and a suitable solvent to form an intermediate compound VII;

wherein X is a halogen in compound VII; the halogenating reagent is selected from phosphorus oxychloride, phosphorus tribromide or phosphorus pentachloride; the base is selected from triethylamine, diisopropylethylamine, DBU, dimethylaminopyridine or N,N-dimethylformamide; the solvent is selected from toluene, acetonitrile, dioxane or phosphorus oxychloride; the temperature of the reaction is 50-120° C.;

Step 4: reacting the above intermediate compound VII with compound VI under a base and a suitable solvent to form nintedanib;

wherein the base is triethylamine, diisopropylethylamine, sodium bicarbonate, sodium carbonate or potassium carbonate; the solvent is methanol, ethanol, acetonitrile, N,N-dimethylformamide or 1,4-dioxane; the temperature of the reaction is 20-80° C., preparation process 2

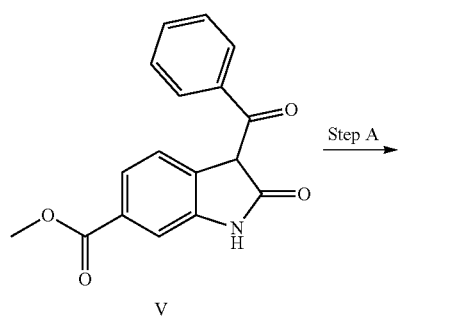

V

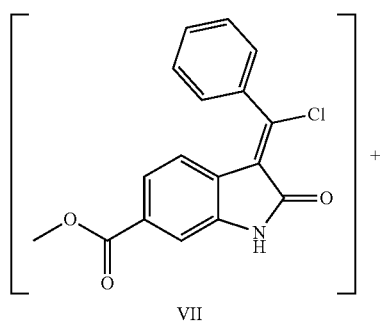

VII

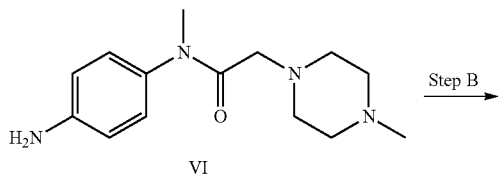

VI

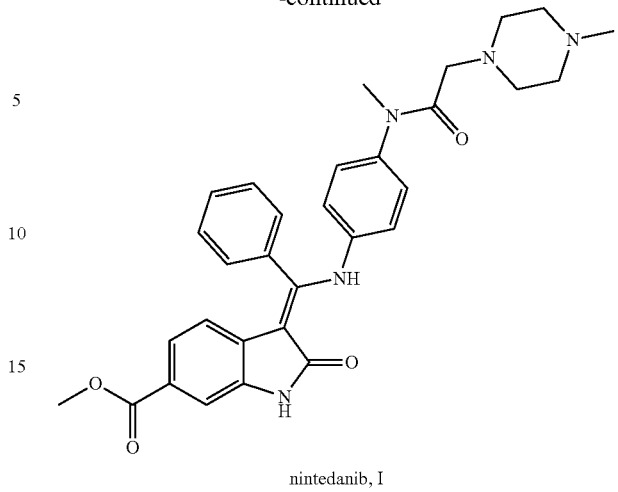

nintedanib, I wherein,

Step A: forming compound VII from compound V in a halogenating agent and a base;

Step B: adding compound VI and a base directly to the system after the reaction of the step A without separation, and reacting to form nintedanib;

wherein the step A is carried out without a solvent or in an organic solvent selected from toluene, acetonitrile or dioxane, wherein the halogenating agent is selected from phosphorus oxychloride, phosphorus pentoxide or phosphorus pentachloride; the base is selected from triethylamine, diisopropylethylamine or DBU;

the step B is carried out in a solvent selected from methanol, ethanol, acetonitrile, tetrahydrofuran or dichloromethane, or a mixed solvent thereof; and the base used is selected from triethylamine, diisopropylethylamine, sodium bicarbonate, sodium carbonate or potassium carbonate.

2. The method according to claim 1, wherein in preparation process 1, X is chlorine or bromine in compounds II and VII; $R_1$ is a C1-C6 alkyl or a C7-C12 aromatic alkyl in compounds III and IV.

3. The method according to claim 1, wherein in preparation process 1, the temperature of the reaction in step 1 is 60-90° C.

4. The method according to claim 1, wherein in preparation process 1, the temperature of the reaction in step 2 is 20-80° C.

5. The method according to claim 1, wherein in preparation process 1, the temperature of the reaction in step 3 is 60-100° C.

6. The method according to claim 1, wherein in preparation process 1, the temperature of the reaction in step 4 is 50-70° C.

7. The method according to claim 2, wherein in preparation process 1, $R_1$ is a methyl or an ethyl in compounds III and IV.

* * * * *